(12) United States Patent
Wang et al.

(10) Patent No.: US 11,955,225 B2
(45) Date of Patent: Apr. 9, 2024

(54) APPARATUS AND METHOD FOR PROVIDING DIETARY RECOMMENDATION

(71) Applicant: KONINKLIJKE PHILIPS N.V., Eindhoven (NL)

(72) Inventors: Lu Wang, Eindhoven (NL); Ming Zhang, Eindhoven (NL); Adrienne Heinrich, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 116 days.

(21) Appl. No.: 17/633,614

(22) PCT Filed: Aug. 3, 2020

(86) PCT No.: PCT/EP2020/071755
§ 371 (c)(1),
(2) Date: Feb. 8, 2022

(87) PCT Pub. No.: WO2021/023689
PCT Pub. Date: Feb. 11, 2021

(65) Prior Publication Data
US 2022/0319667 A1 Oct. 6, 2022

(30) Foreign Application Priority Data
Aug. 8, 2019 (EP) .................................. 19190777

(51) Int. Cl.
*G06F 16/00* (2019.01)
*G06F 16/904* (2019.01)
(Continued)

(52) U.S. Cl.
CPC ........... *G16H 20/60* (2018.01); *G06F 16/904* (2019.01); *G06F 16/908* (2019.01)

(58) Field of Classification Search
CPC .......... G06F 1/163; G06F 3/011; G06F 3/017; G06F 1/1686; G06F 1/1694;
(Continued)

(56) References Cited

U.S. PATENT DOCUMENTS 7,974,881 B2   7/2011   Culver et al.
8,626,796 B2   1/2014   McBride et al.
(Continued)

FOREIGN PATENT DOCUMENTS

CA    2988127 A1    12/2016
WO    2015001595 A1   1/2015
(Continued)

OTHER PUBLICATIONS

"Health Effects of Overweight and Obesity in 195 Countries over 25 years", The GBD 2015 Obesity Collaborators, The New England Journal of Medicine, vol. 377, Issue 1, pp. 13-27, Jul. 6, 2017.
(Continued)

*Primary Examiner* — Shyue Jiunn Hwa
(74) *Attorney, Agent, or Firm* — Maschoff Brennan (57) ABSTRACT

A method for providing dietary recommendation for a subject includes acquiring a dietary target for the subject, acquiring data associated with dietary consumption of the subject, and determining a balance score based on the acquired dietary target and the acquired data associated with dietary consumption of the subject. The method further includes acquiring a plurality of meal options for the subject, where each of the plurality of meal options is representative of a suggested meal, determining a salience score for each of the plurality of meal options, where the determination is based on the dietary target, dietary information of the respective meal option, and the determined balance score,
(Continued)

and generating a personalized dietary recommendation for the subject based on at least one of the determined salience scores.

19 Claims, 5 Drawing Sheets

(51) Int. Cl.
*G06F 16/908* (2019.01)
*G16H 20/60* (2018.01)

(58) Field of Classification Search
CPC .... G06F 1/3215; G06F 1/3278; G06F 1/3287; G06F 16/367; G06F 16/9535; G06F 3/013; G06F 3/015; G06F 3/016; G06F 3/0304; G06F 3/0346; G06F 40/137; G06F 40/216; G06F 40/284; G06F 40/295; G06F 40/30; G06F 40/35; G06F 16/335; G06F 16/90324; G06F 16/9035; G06F 18/00; G06F 18/22; G06F 18/23213; G06F 18/2411; G06F 3/0482; G16H 20/60; G16H 20/30; G09B 19/0092; A23L 33/30
See application file for complete search history.

(56) References Cited

U.S. PATENT DOCUMENTS

| | | | |
|---|---|---|---|
| 9,011,153 | B2 | 4/2015 | Bennett et al. |
| 2009/0148818 | A1 | 6/2009 | Li et al. |
| 2010/0003647 | A1 | 1/2010 | Brown et al. |
| 2010/0111383 | A1 | 5/2010 | Boushey et al. |
| 2011/0009708 | A1 | 1/2011 | Boyes |
| 2012/0083669 | A1 | 4/2012 | Abujbara |
| 2013/0216982 | A1 | 8/2013 | Bennett et al. |
| 2015/0161910 | A1 | 6/2015 | Bailor |
| 2016/0063692 | A1 | 3/2016 | Divakaran et al. |
| 2016/0103834 | A1 | 4/2016 | Altaf et al. |
| 2017/0069225 | A1 | 3/2017 | Ortiz et al. |
| 2017/0193853 | A1 | 7/2017 | Byron et al. |
| 2018/0144820 | A1* | 5/2018 | Grimmer ............... G16H 20/60 |
| 2019/0228856 | A1 | 7/2019 | Leifer et al. |
| 2019/0295440 | A1* | 9/2019 | Hadad .................. G06F 40/295 |

FOREIGN PATENT DOCUMENTS

| | | |
|---|---|---|
| WO | 2016065463 A1 | 5/2016 |
| WO | 2018099838 A1 | 6/2018 |

OTHER PUBLICATIONS

Benjamin-Neelon, S. E., et al., "The Family Child Care Home Environment and Children's Diet Quality", Appetite, vol. 126, pp. 108-113, Jul. 2018.

Extended European Search Report issued in connection with corresponding EP Application No. 19190777.3 dated Jun. 23, 2020.

International Search Report and Written Opinion issued in connection with corresponding PCT Application No. PCT/EP2020/071755 dated Oct. 12, 2020.

* cited by examiner

APPARATUS AND METHOD FOR PROVIDING DIETARY RECOMMENDATION

CROSS-REFERENCE TO RELATED APPLICATIONS

The present application is a U.S. National Phase application under 35 U.S.C. § 371 of International Application No. PCT/EP2020/071755, filed on Aug. 3, 2020, which claims the benefit of European Patent Application No. 19190777.3, filed on Aug. 8, 2019. These applications are hereby incorporated by reference herein.

FIELD OF THE INVENTION

The present disclosure relates to an apparatus and method for providing dietary recommendation for a subject.

BACKGROUND OF THE INVENTION

Children today, as studies have shown, are increasingly overweight due to habits that start when they are young in response to an environment that promotes routines and eating patterns which, in the long run, are injurious to their health. One of the main reasons of the growing rates of childhood obesity in developed countries is the increased availability of energy-dense food. Although it is common knowledge that a healthy diet can significantly reduce the risk of diseases such as diabetes and chronic kidney disease, many children do not yet have the understanding, willpower, or control in terms of consuming a balanced diet.

Studies have shown that nutrition education can lead to better and healthier eating habits. Therefore, it is important to provide education regarding meal planning to children while they are at a young age.

SUMMARY OF THE INVENTION

As noted above, there is a demand for an approach to provide nutrition and meal planning education to young children. It is important to take into account of both the objective of achieving a balanced diet as well as motivating users (e.g. children) by considering their subjective preferences. It is also important to allow users to foresee the consequences of selecting a certain food item or a certain meal during meal planning. The present disclosure proposes a method and an apparatus that present possible meal options and a degree of balance (which is indicative of how close the user is to achieving their health-related target) by adapting to user input, context information, as well as short-term and long-term food intake history. The proposed method also includes determining salience score for possible food options which define how meal options are presented to a user. Although parts of the present disclosure may include description with reference to the subject and/or user being a young child, it will be appreciated that the proposed method can also be used for the purpose of nutrition education and meal planning by/for adults.

According to a first aspect of the present disclosure, a computer-implemented method for providing dietary recommendation for a subject is provided. The method comprises: acquiring a dietary target for the subject, wherein the dietary target is indicative of at least one of a target amount of a nutrient type and a target amount of dietary energy to be consumed by the subject in a periodic interval; acquiring data associated with dietary consumption of the subject; determining a balance score based on the acquired dietary target and the acquired data associated with dietary consumption of the subject, wherein the balance score is indicative of a difference between a current dietary progress of the subject and the acquired dietary target; acquiring a plurality of meal options for the subject, wherein each of the plurality of meal options is representative of a suggested meal and comprises dietary information associated with at least one of: an amount of dietary energy of the respective meal option and an amount of nutrient type of the respective meal option, wherein the nutrient type corresponds to the nutrient type in the dietary target; determining a salience score for each of the plurality of meal options, wherein the determination is based on the dietary target, the dietary information of the respective meal option, and the determined balance score; and generating a personalized dietary recommendation for the subject based on at least one of the determined salience scores, wherein the personalized dietary recommendation is associated with at least one of the plurality of meal options.

In some embodiments, the method may further comprise controlling a display device to output a visual representation of the generated personalized dietary recommendation for the subject.

In some embodiments, controlling the display device to output a visual representation of the personalized dietary recommendation may comprise controlling the display device to output more than one of the plurality of meal options.

In some embodiments, the more than one of the plurality of meal options may be outputted such that at least one of the following is in accordance with the salience score of the respective meal option: a relative order of the displayed meal option, a relative level of color saturation of the displayed meal option, and a relative size of the displayed meal option.

In some embodiments, the method may further comprise: receiving a user input selecting a meal option from the displayed meal options; determining an updated balance score based on the dietary information of the selected meal option; determining an updated salience score for each of the plurality of acquired meal options; and generating an updated personalized dietary recommendation for the subject based on at least one of the updated salience scores.

In some embodiments, the method may further comprise ranking the plurality of meal options based on the determined salience scores. In these embodiments, generating the personalized dietary recommendation for the subject may be based on the ranking of the plurality of meal options.

In some embodiments, each of the plurality of meal options may further comprise information associated with at least one of: one or more food ingredients in the meal option and one or more food types in the meal option. In these embodiments, the method may further comprise receiving a user input indicating at least one of a food ingredient preference of the subject and a food type preference of the subject, and determining the salience score for each of the plurality of acquired meal options may be based on the received user input and the information associated with at least one of: one or more food ingredients in the meal option and one or more food types in the meal option.

In some embodiments, generating the personalized dietary recommendation for the subject may comprise: selecting one or more of the plurality of meal options based on the determined salience scores of the respective meal options; and acquiring, for each of the one or more selected meal options, a recipe containing instructions for preparing the respective meal option, and wherein controlling the display device to output a visual representation of the personalized dietary recommendation comprises controlling the display device to output the one or more acquired recipes.

In some embodiments, the method may further comprise: acquiring updated data associated with dietary consumption of the subject; determining an updated balance score based on the dietary target and the updated data associated with dietary consumption of the subject; and controlling a display device to output a visual representation of the initial balance score and the updated balance score.

In some embodiments, the method may further comprise: acquiring context information associated with at least one of: one or more locations of the subject in the current periodic interval and one or more activities of the subject in the current periodic interval; receiving a user input indicating a flexibility value, wherein the flexibility value is indicative of a relative degree of user-intended allowed deviation of the dietary consumption of the subject in the current periodic interval from the dietary target; and determining a tolerance value for the current period interval based on the dietary target, the flexibility value, the acquired context information, and the balance score, wherein the tolerance value is indicative of an amount of allowed deviation of the dietary consumption of the subject in the current periodic interval from the dietary target. In these embodiments, the determination of a salience score for each of the plurality of meal options may be further based on the tolerance value.

In some embodiments, acquiring the dietary target for the subject may comprise: acquiring the age of the subject and data associated with the body mass index of the subject; receiving a user input indicating a health objective of the subject; and determining the dietary target for the subject based on the age of the subject, data associated with the body mass index of the subject, and the health objective of the subject.

In some embodiments, acquiring the dietary target for the subject may comprise: acquiring the age of the subject and data associated with the body mass index of the subject; retrieving, from a database, a standard dietary target for a subject having the same age and body mass index of the subject; and setting the received standard dietary target as the dietary target for the subject.

In some embodiments, acquiring data associated with dietary consumption of the subject may comprise: acquiring an image depicting a food item consumed by the subject; performing an image recognition process on the acquired image to identify the food item consumed by the subject; and estimating at least one of an amount of dietary energy and an amount of nutrient type of the identified food item.

According to a second aspect, there is provided a computer program product comprising a computer readable medium, the computer readable medium having computer readable code embodied therein, the computer readable code being configured such that, on execution by a suitable computer or processor, the computer or processor is caused to perform the method as described herein.

According to a third aspect, an apparatus for providing dietary recommendation for a subject, the apparatus comprising a processor configured to: acquire a dietary target for the subject, wherein the dietary target is indicative of at least one of a target amount of a nutrient type and a target amount of dietary energy to be consumed by the subject in a periodic interval; acquire data associated with dietary consumption of the subject; determine a balance score based on the acquired dietary target and the acquired data associated with dietary consumption of the subject, wherein the balance score is indicative of a difference between a current dietary progress of the subject and the acquired dietary target; acquire a plurality of meal options for the subject, wherein each of the plurality of meal options is representative of a suggested meal and comprises dietary information associated with at least one of: an amount of dietary energy of the respective meal option and an amount of nutrient type of the respective meal option, wherein the nutrient type corresponds to the nutrient type in the dietary target; determine a salience score for each of the plurality of meal options, wherein the determination is based on the dietary target, the dietary information of the respective meal option, and the determined balance score; and generate a personalized dietary recommendation for the subject based on at least one of the determined salience scores, wherein the personalized dietary recommendation is associated with at least one of the plurality of meal options.

According to the aspects and embodiments described above, the limitations of existing dietary recommendation techniques are addressed. In particular, the above-described aspects and embodiments enable dietary recommendation that take into account both objective health goals and subjective preferences. The embodiments described above offer a way to present food options to users that prioritize food options that align with the health objective of the user and are also appealing to the user. In this way, the embodiments as described in the present disclosure allow personalized dietary recommendation to be provided in order to maximize the effectiveness of the recommendation as well as a likeliness of the user to adhere to the recommendation.

There is thus provided an improved method and apparatus for providing dietary recommendation for a subject. These and other aspects of the disclosure will be apparent from and elucidated with reference to the embodiment(s) described hereinafter.

BRIEF DESCRIPTION OF THE DRAWINGS

For a better understanding of the embodiments, and to show more clearly how they may be carried into effect, reference will now be made, by way of example only, to the accompanying drawings, in which.

DETAILED DESCRIPTION OF EMBODIMENTS

As noted above, there is provided an improved apparatus and a method of operating the same which addresses the existing problems.

Figure 1:
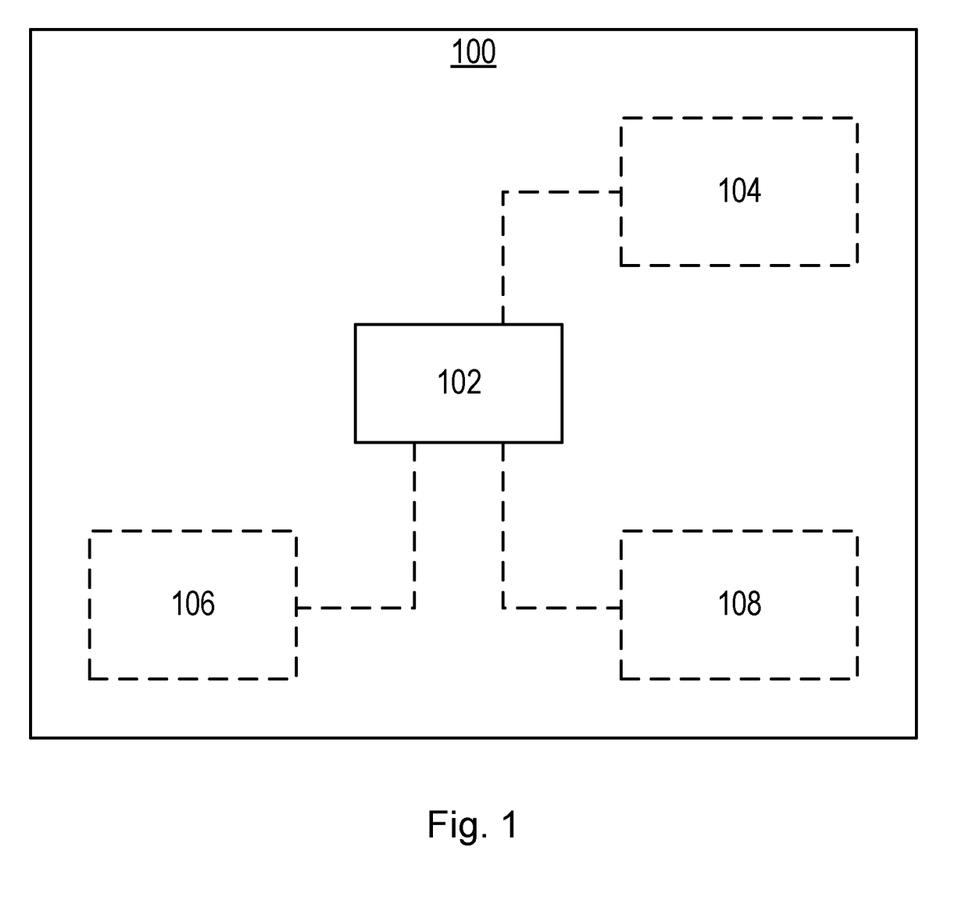
FIG. 1 is a block diagram of an apparatus for providing dietary recommendation for a subject, according to an embodiment.

FIG. 1 shows a block diagram of an apparatus 100 according to an embodiment, which can be used for providing dietary recommendation for a subject. Although the operation of the apparatus 100 is described below in the context of a single subject, it will be appreciated that the apparatus 100 is capable of providing dietary recommendations for a plurality of subjects.

As illustrated in FIG. 1, the apparatus comprises a processor 102 that controls the operation of the apparatus 100 and that can implement the method described herein. The processor 102 can comprise one or more processors, processing units, multi-core processor or modules that are configured or programmed to control the apparatus 100 in the manner described herein. In particular implementations, the processor 102 can comprise a plurality of software and/or hardware modules that are each configured to perform, or are for performing, individual or multiple steps of the method described herein.

Briefly, the processor 102 is configured to acquire a dietary target for the subject, the dietary target being indicative of at least one of a target amount of a nutrient type and a target amount of dietary energy to be consumed by the subject in a periodic interval. The processor 102 is also configured to acquire data associated with dietary consumption of the subject, and to determine a balance score based on the acquired dietary target and the acquired data associated with dietary consumption of the subject. The balance score is indicative of a difference between a current dietary progress of the subject and the acquired dietary target. Moreover, the processor 102 is configured to acquire a plurality of meal options for the subject, each of the plurality of meal options being representative of a suggested meal and comprising dietary information associated with at least one of: an amount of dietary energy of the respective meal option and corresponds to the nutrient type in the dietary target.

The processor 102 is further configured to determine a salience score for each of the plurality of meal options and generate a personalized dietary recommendation for the subject. The determination of the salience scores is based on the dietary target, the dietary information of the respective meal option, and the determined balance score; the generation of the personalized dietary recommendation for the subject is based on at least one of the determined salience scores. The personalized dietary recommendation is associated with at least one of the plurality of meal options.

In some embodiments, the apparatus 100 may further comprise at least one user interface 104. Alternative or in addition, at least one user interface 104 may be external to (i.e. separate to or remote from) the apparatus 100. For example, at least one user interface 104 may be part of another device. A user interface 104 may be for use in providing a user of the apparatus 100 with information resulting from the method described herein. Alternatively or in addition, a user interface 104 may be configured to receive a user input. For example, a user interface 104 may allow a user of the apparatus 100 to manually enter instructions, data, or information. In these embodiments, the processor 102 may be configured to acquire the user input from one or more user interfaces 104.

A user interface 104 may be any user interface that enables the rendering (or output or display) of information to a user of the apparatus 100. Alternatively or in addition, a user interface 104 may be any user interface that enables a user of the apparatus 100 to provide a user input, interact with and/or control the apparatus 100. For example, the user interface 104 may comprise one or more switches, one or more buttons, a keypad, a keyboard, a touch screen or an application (for example, on a tablet or smartphone), a display screen, a graphical user interface (GUI) or other visual rendering component, one or more speakers, one or more microphones or any other audio component, one or more lights, a component for providing tactile feedback (e.g. a vibration function), or any other user interface, or combination of user interfaces.

In some embodiments, the apparatus 100 may comprise a memory 106. Alternatively or in addition, one or more memories 106 may be external to (i.e. separate to or remote from) the apparatus 100. For example, one or more memories 106 may be part of another device or implemented in a cloud infrastructure. A memory 106 can be configured to store program code that can be executed by the processor 102 to perform the method described herein. A memory can be used to store information, data, signals and measurements acquired or made by the processor 102 of the apparatus 100. For example, a memory 106 may be used to store (for example, in a local file) the data associated with dietary consumption of the subject, and/or the determined balance score, and/or the determined salience scores. The processor 102 may be configured to control a memory 106 to store the data associated with dietary consumption of the subject, and/or the determined balance score, and/or the determined salience scores.

In some embodiments, the apparatus 100 may comprise a communications interface (or circuitry) 108 for enabling the apparatus 100 to communicate with any interfaces, memories and/or devices that are internal or external to the apparatus 100. The communications interface 108 may communicate with any interfaces, memories and/or devices wirelessly or via a wired connection. For example, the communications interface 108 may communicate with one or more user interfaces 104 wirelessly or via a wired connection. Similarly, the communications interface 108 may communicate with the one or more memories 106 wirelessly or via a wired connection.

It will be appreciated that FIG. 1 only shows the components required to illustrate an aspect of the apparatus 100 and, in a practical implementation, the apparatus 100 may comprise alternative or additional components to those shown.

Figure 2:
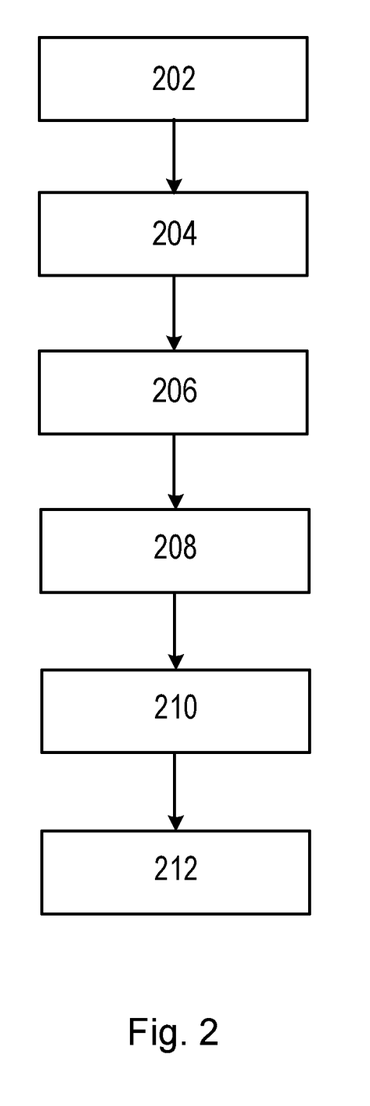
FIG. 2 illustrates a method for providing dietary recommendation for a subject, according to an embodiment.

FIG. 2 illustrates a computer-implemented method for providing dietary recommendation for a subject, according to an embodiment. The illustrated method can generally be performed by or under the control of processor 102 of the apparatus 100. In some embodiments, the illustrated method may be implemented as an application software on a smartphone or a tablet (or any similar devices). In other embodiments, the illustrated method may be implemented on a cloud infrastructure.

With reference to FIG. 2, at block 202, a dietary target for the subject is acquired. Specifically, the dietary target may be acquired by the processor 102 of the apparatus 100. The dietary target is indicative of a target amount of a nutrient type and a target amount of dietary energy to be consumed by the subject in a periodic interval (e.g. a day or a week).

Moreover, in some embodiments, acquiring the dietary target for the subject may comprise: acquiring the age of the subject and data associated with the body mass index of the subject, receiving a user input indicating a health objective of the subject, and determining the dietary target for the subject based on the age of the subject, data associated with the body mass index of the subject, and the health objective of the subject. For example, a user (e.g. the subject himself/herself) may indicate via a user input that the health objective of the subject is to "lose 2 kg within 6 months". Based on this health objective and also the age of the subject as well as the data associated with the body mass index of the subject (and further optionally the gender of the subject), a dietary target for the subject (e.g. consume less than 1800 kcal per day) may be determined. In some embodiments, the data associated with the body mass index of the subject may include at least one of: the body mass index of the subject, the weight of the subject, and the height of the subject. Furthermore, the acquired dietary target may be adapted periodically or upon receiving a trigger for adaptation. For example, if the health objective of the subject is to "lose 2 kg within 6 months" and the subject has not lost weight for the first 3 months, a trigger may be used to cause adaptation of the dietary target (e.g. reducing the weekly dietary target for dietary energy consumption from 7000 calories to 6000 calories).

In some alternative embodiments, acquiring the dietary target for the subject may comprise: acquiring the age of the subject and data associated with the body mass index of the subject, retrieving, from a database (e.g. a public knowledgebase like WebMD), a standard dietary target for a subject having the same age and body mass index of the subject, and setting the received standard dietary target as the dietary target for the subject. For example, the standard calorie daily target for a sedentary child between 2 and 3 years old may be around 1000 calories. Furthermore, the method may comprise acquiring the gender of the subjects, and the retrieval of the standard dietary target may be further based on the gender of the subject.

In some alternative embodiments, acquiring the dietary target for the subject may comprise receiving a user input setting the dietary target for the subject.

Returning to FIG. 2, at block 204, data associated with dietary consumption of the subject is acquired. Specifically, the data associated with dietary consumption of the subject may be acquired by the processor 102 of the apparatus 100. In some embodiments, the data associated with dietary consumption of the subject may be acquired in real time. The data associated with dietary consumption of the subject may comprise at least one of: a type of a food item consumed by the subject (e.g. "pizza"), an amount of food item consumed by the subject (e.g. "1 slice", or "300 g"), an amount of nutrient type in the food item consumed by the subject, and an amount of dietary energy in the food item consumed by the subject.

In some embodiments, data associated with dietary consumption of the subject may be acquired through user input, for example a user selection of a recipe which contains information regarding the amount of dietary energy and/or nutrients of the meal associated with the recipe, where the user selection indicates that the subject has consumed or will consume in the current periodic interval the corresponding meal prepared using the recipe.

Alternatively or in addition, in some embodiments, acquiring data associated with dietary consumption of the subject may comprise: acquiring an image depicting a food item consumed by the subject in the current periodic interval (or to be consumed by the subject in the current periodic interval), performing an image recognition process on the acquired image to identify the food item consumed by the subject in the current periodic interval (or to be consumed by the subject in the current periodic interval), and estimating at least one of an amount of dietary energy and an amount of nutrient type of the identified food item.

Alternatively or in addition, in some embodiments, the data associated with dietary consumption of the subject may be acquired from a public reference database (e.g. United States Department of Agriculture Food Composition Databases).

Returning to FIG. 2, at block 206, a balance score is determined based on the dietary target acquired at block 202 and the data associated with dietary consumption of the subject acquired at block 204. The balance score is indicative of a difference between a current dietary progress of the subject and the acquired dietary target. The balance score may be determined by the processor 102 of the apparatus 100.

In some embodiments, the method may comprise acquiring updated data associated with dietary consumption of the subject. For example, the subject may indicate via a user input that they have just consumed a meal and the food ingredients in the meal. In these embodiments, the balance score may be determined and updated, e.g. in real time, based on the data associated with dietary consumption of the subject acquired at block 204. For example, a new balance score may be determined according to the updated data associated with the dietary consumption of the subject and the dietary target. In other embodiments, the balance score may be updated periodically, e.g. per hour or per day depending on the length of the periodic interval used.

In some embodiments where more than one balance scores have been determined (e.g. an initial balance score and an updated balance score), the method may further comprise controlling a display device to output a visual presentation of at least the initial balance score and the updated balance score. For example, as will be explained in more detail with reference to FIG. 3E, in some embodiments the change in balance score throughout a current periodic interval may be visually represented at a virtual user interface (e.g. one that can be displayed via a smartphone device) so as to allow a user (e.g. the subject) to review the current balance score as well as the historical variation in the balance score.

In some embodiments, the balance score may be determined based on the food intake I of the subject during the past n days (which may be at least part of the data associated with dietary consumption of the subject), which is represented by $I_{t-n}, \ldots, I_{t-1}, I_t$, and the dietary target G for the subject the past n days, which is represented by $G_{t-n}, \ldots, G_{t-1}, G_t$. Specifically, the balance score $B_t$ on day t may be determined based on the following equations (1) or (2):

$$B_t = \Sigma_{i=0}^{n} G_{t-n} - I_{t-n}, \text{ if the dietary target relates to reducing nutrient/energy intake} \quad (1)$$

$$B_t = \Sigma_{i=0}^{n} I_{t-n} - G_{t-n}, \text{ if the dietary target relates to increasing nutrient/energy intake} \quad (2)$$

Based on the equations above, the determined balance score in these embodiments may fluctuate around 0, with a negative value indicating that the subject has not reached their dietary target and a positive value indicating that the subject has exceed their dietary target.

Returning to FIG. 2, at block 208, a plurality of meal options for the subject is acquired. Specifically, the plurality of meal options for the subject may be acquired by the processor 102 of the apparatus 100. Each of the plurality of meal options is representative of a suggested meal, and comprises dietary information associated with at least one of: an amount of dietary energy of the respective meal option and an amount of nutrient type of the respective mal option. The nutrient type in this context corresponds to the nutrient type in the dietary target acquired at block 202. For example, if the dietary target acquired at block 202 is indicative of a target amount of protein to be consumed by the subject in a periodic interval, each of the plurality of meal options may comprise dietary information associated with an amount of protein of the respective meal.

In some embodiments, the plurality of meal options for the subject may be acquired from a database containing a plurality of candidate meal options. In these embodiments, the plurality of meal options for the subject may be extracted from the database based on the balanced score determined at block 206 and the dietary information (e.g. an amount of dietary energy and/or an amount of nutrient type) of the candidate meal options.

Returning to FIG. 2, at block 210, a salience score is determined for each of the plurality of meal options acquired at block 208. Specifically, the salience scores may be determined by the processor 102 of the apparatus 100. The determination at block 210 is based on the dietary target acquired at block 202, the dietary information of the respective meal option, and the balance score determined at block 206.

In some embodiments, each of the plurality of meal options for the subject may comprise information associated with at least one of: one or more food ingredients in the meal option and one or more food types in the meal option. In these embodiments, the method may further comprise receiving a user input indicating at least one of a food ingredient preference of the subject and a food type preference of the subject, and the determination of the salience scores at block 210 may be on the received user input and the information associated with at least one of: one or more food ingredients in the meal option and one or more food types in the meal option. For example, a food ingredient preference of the subject may be "beef", and in this case the salience score of a meal option that includes beef as a food ingredient may have a higher salience score than a similar meal option that does not include beef (e.g. beef noodle compared with chicken noodle). As another example, a food type preference of the subject may be "pizza", and in this case the salience score of a meal option that includes pizza may have a higher salience score than other possible meal options.

Although it is described above that in some embodiments the method may further comprise receiving a user input indicating at least one of a food ingredient preference of the subject and a food type preference of the subject, in alternative embodiments the at least one of a food ingredient preference of the subject and a food type preference of the subject may be determined using machine learning techniques. For example, a predictive model may be trained using data associated with the dietary consumption of the subject and/or data associated with the dietary preferences of the subject, and at least one of a food ingredient preference of the subject and a food type preference of the subject may be determined based on the trained predictive model.

In some embodiments, the method may further comprise acquiring context information associated with at least one of: one or more locations of the subject in the current periodic interval and one or more activities of the subject in the current periodic interval. For example, the context information may include a type of exercise and/or a duration of exercise performed by the subject in the current periodic interval. As another example, the context information may include a type of activity (such as sitting, standing, or walking) and a corresponding duration of the activity. As yet another example, context information may indicate whether the subject is currently at a restaurant, or whether the subject is currently on vacation. As yet another example, context information may indicate whether the current periodic interval coincides with a personal special occasion (e.g. birthdays, special holidays, etc.). Moreover, context information may indicate a current time during the current periodic interval (e.g. morning). In some embodiments, the context information may be acquired from an activity tracking device and/or received as a user input. Context information associated with one or more activities of the subject may comprise a total activity level of the subject in the current periodic interval or an activity level of an activity performed by the subject in the current periodic level. The activity level may be categorized as one of "very active", "moderately active", and "sedentary" on the basis of predetermined ranges or thresholds.

In these embodiments, the method may comprise receiving a user input indicating a flexibility value, the flexibility value being indicative of a relative degree of user-intended allowed deviation of the dietary consumption of the subject in the current periodic interval from the dietary target. For example, a user input indicating one of "low flexibility", "medium flexibility", and "high flexibility", which can then be converted into corresponding predetermined flexibility values. Furthermore, in some embodiments the flexibility value may take a value between 0 and 1. As an example, a user can set "low flexibility, i.e. lower relative degree of allowed deviation of the dietary consumption of the subject in the current periodic interval from the dietary target, which can be converted to a flexibility value of 0.2; similarly a user can set "high flexibility", i.e. higher relative degree of allowed deviation of the dietary consumption of the subject in the current periodic interval from the dietary target, which can be converted to a flexibility value of 0.8. The method may also comprise determining a tolerance value for the current period interval, the tolerance value being indicative of an amount of allowed deviation of the dietary consumption of the subject from the dietary target. The determination may be based on the dietary target, the flexibility value indicated in the received user input, the acquired context information, and the balance score. For example, when the flexibility value is low, e.g. 0.2, the tolerance value can be determined accordingly such that it has a relatively lower value, and when the flexibility value is high, e.g. 0.8, the tolerance value can be determined such that it has a relatively higher value. Moreover, in these embodiments, the determination of a salience score for each of the plurality of meal options at block 210 may be further based on the tolerance value.

As described above with reference to the determination of the balance value, in some embodiments, the balance value may be determined based on the food intake I of the subject and the dietary target G for the subject. In these embodiments, the tolerance value $Tol_t$ on day t may be determined based on the following equation:

$$Tol_t = G_t F + \sum_{i=0}^{n} K(a_m) + B_t \qquad (3)$$

In the above equation, $G_t$ represents the dietary target on day t (which is indicative of at least one of a target amount of a nutrient type and a target amount of dietary energy to be consumed by the subject in a day), F represents the flexibility value, $K(a_m)$ represents a tolerance increment for the activity $a_m$, for example an activity a="birthday" would increase the tolerance value by K(birthday)=1000 calories.

An exemplary embodiment in which the dietary target acquired at block 202 is indicative of a target amount of dietary energy to be consumed by the subject in a day and the health objective of the subject is to reduce intake of dietary energy is outlined below to illustrate the determination of salience scores in more detail. In this example, as the health objective of the subject is to reduce intake of dietary energy, the salience score $S_m$ for a meal option m may be determined based on the equations below:

$$S_m = Tol_t - K_{cal}(m) \quad (4)$$

$$S_m = (Tol_t - K_{cal}(m))(1 + r_{ig}|IG_u \cap K_{ig}(m)| + r_{tp}|TP_u \cap K_{tp}(m)|) \quad (5)$$

where $IG_u = \{ig_1, ig_2, \ldots, ig_n\}$, and $TP_u = \{tp_1, tp_2, \ldots, tp_n\}$ In the above equations, $Tol_t$ represents the tolerance value on day t, $K_{cal}(m)$ represents the amount of dietary energy (in calories) of meal option m, $r_{ig}$ represents a food ingredient recommendation factor which defines the percentage increase of the salience score if a food ingredient contained in the respective meal option matches the food ingredient preference of the subject, $IG_u$ represents the food ingredient preferences $\{ig_1, ig_2, \ldots, ig_n\}$ of subject u, for example "chicken" and "potato", $K_{ig}(m)$ represents the food ingredients of the meal option m, $r_{tp}$ represents a food type recommendation factor which defines the percentage increase of the salience score if a food type of the respective meal option matches the food type preference of the subject, $TP_u$ represents the food type preferences $\{tp_1, tp_2, \ldots, tp_n\}$ of the subject u, for example "fried food" or "ice cream", and $K_{tp}(m)$ represents the food type of the meal option m.

As described above, the determination of the salience score of a respective meal option may optionally be based on a food ingredient preference of the subject and/or a food type preference of the subject. Therefore, in some embodiments the salience score may be determined based on equation (4), especially when the method does not include receiving user input indicating the food ingredient/type preference of the subject, while in other embodiments the salience score may be determined based on equation (5).

As mentioned above, in some embodiments the balance score may be determined and updated (e.g. in real time) based on the data associated with dietary consumption of the subject acquired at block 204. In these embodiments, a new tolerance score may also be determined based on the updated balance score. The determination of the new tolerance score may be triggered by an update of the balance score or performed periodically.

By taking into account the tolerance value (which is indicative of an amount of allowed deviation of the dietary consumption of the subject from the dietary target) in the determination of salience scores, the generation of the personalized dietary recommendation at block 212 can be further tailored based on context (e.g. environment and/or activity of the subject in the current periodic interval) as well as a current progress of the subject with respect to the dietary target.

Returning to FIG. 2, at block 212, a personalized dietary recommendation for the subject is generated based on at least one of the salience scores determined at block 210. The generated personalized dietary recommendation is associated with at least one of the plurality of meal options. The personalized dietary recommendation for the subject may be generated by the processor 102 of the apparatus 100.

In some embodiments, the method may further comprise ranking the plurality of meal options based on the determined salience scores. In these embodiments at block 212 the generation of the personalized dietary recommendation may be based on the ranking of the plurality of meal options.

In some embodiments, the method may further comprise controlling a display device to output a visual representation of the personalized dietary recommendation for the subject generated at block 212. In these embodiments, controlling the display device to output the visual representation of the personalized dietary recommendation may comprise controlling the display device to output more than one of the plurality of meal options acquired at block 208. More specifically, the more than one of the plurality of meal options may be outputted such that at least one of the following is in accordance with the salience score of the respective meal option: a relative order of the displayed meal option, a relative level of color saturation of the displayed meal option, and a relative size of the displayed meal option. In some embodiments, a degree of playfulness of the displayed meal option may be dependent on the salience score of the respective meal option. For example, for meal options with higher salience score, videos of the respective meal options may be displayed instead of static images to increase their degree of playfulness. Furthermore, in some embodiments, the number of meal options outputted may be based on the respective salience scores of the respective meal options, for example only meal options having salience scores over a predetermined threshold are outputted.

In some embodiments, generation of the personalized dietary recommendation at block 212 may comprise: selecting one or more of the plurality of meal options based on the determined salience scores of the respective meal options, and acquiring, for each of the one or more selected meal options, a recipe containing instructions for preparing the respective meal option. In these embodiments, controlling a display device to output a visual representation of the personalized dietary recommendation may comprise controlling the display device to output the one or more acquired recipes.

In some embodiments, the method may further comprise receiving a user input selecting a meal option from the displayed meal options. For example, a subject may select one of the displayed meal options as an indication of their intention to prepare and consume the meal option. In these embodiments, the method may further comprise determining an updated balance score based on the dietary information of the selected option. This determination may be based on the assumption that the subject will consume or has consumed the selected meal option. Subsequently, the method may determine an updated salience score for each of the plurality of acquired meal options, based on the updated balance score, the dietary target, and the dietary information of the respective meal option. An updated personalized dietary recommendation for the subject can then be generated based on at least one of the updated salience scores.

Figure 3A:
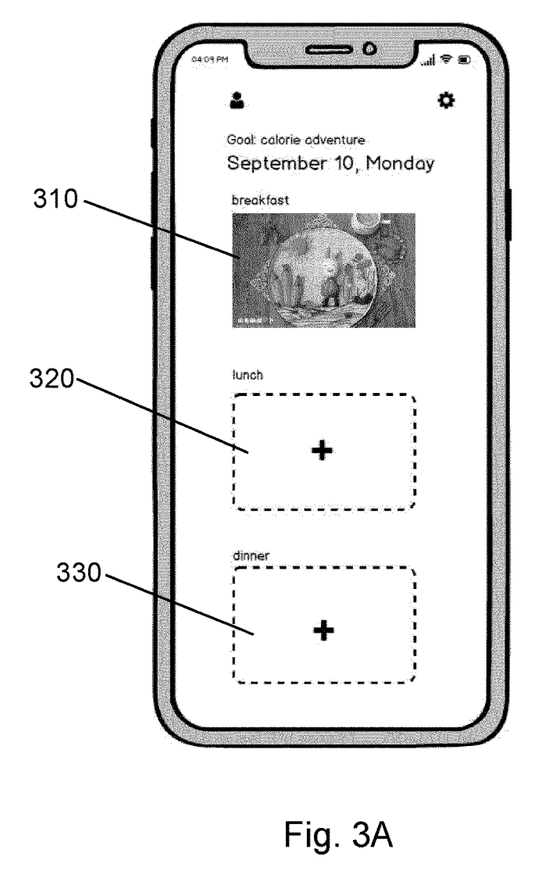
FIG. 3A is an exemplary drawing of the method of FIG. 2 being implemented in a smartphone device.

FIG. 3A to FIG. 3E are exemplary drawings of the method of FIG. 2 being implemented in a smartphone device. In more detail, FIG. 3A shows a home screen of a virtual user interface in accordance to the method as illustrated in FIG. 2. The home screen displays a health objective "Goal: calorie adventure", which indicates that the dietary target is indicative of a target amount of dietary energy (calories) to be consumed by the subject in a periodic interval (day) as well as the current periodic interval ("September 10, Monday"). The virtual user interface may be used by a young child to plan his/her daily meals, including breakfast 310, lunch 320, and dinner 330. As shown in the home screen, the breakfast 310 has already been selected/planned, which is indicated by an image of the selected meal option at the corresponding position in the home screen. At the stage illustrated in FIG. 3A, the young child has not yet planned his/her lunch or dinner.

Figure 3B:
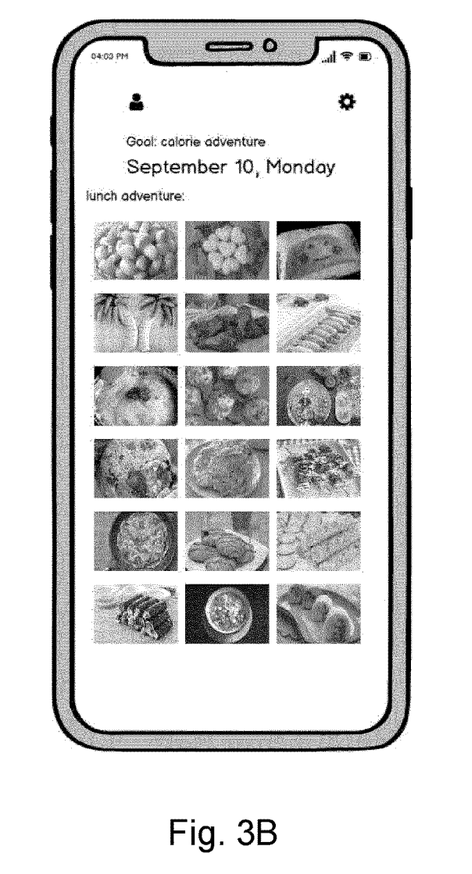
FIG. 3B is another exemplary drawing of the method of FIG. 2 being implemented in a smartphone device.

To select a meal option for his/her lunch of the day, the young child may select the "+" sign at the virtual user interface which corresponds to the lunch 320 of the day. The virtual user interface may then transition to the screen as shown in FIG. 3B which shows a first personalized dietary recommendation for the young child. In this example, the personalized dietary recommendation includes a plurality of possible meal options for lunch, each being represented by an image of the meal option in an image gallery.

As described above with reference to FIG. 2, the plurality of meal options, specifically the images corresponding to each of the plurality of meal options, may be displayed in accordance to their respective salience scores. In this example, the relative placement of an image of a meal option may be dictated by the salience score of the corresponding meal option. In other words, the image of the meal option with the highest salience score amongst all the possible meal options may be placed at the top left corner in the image gallery, the image of the meal option with the second highest salience score may be placed in the middle of the top row of the image gallery, and so on and so forth. In this way, meal options with higher salience scores are positioned such that they are more likely to be noticed and therefore selected by the young child. For example, it has been indicated that the young child prefers "chicken wings", and therefore as shown in FIG. 3B the image of the "chicken wings" meal option is placed in the middle of the second row in the image gallery, while the image of the "vegetable salad" meal option is placed in on the right hand side of the third row in the image gallery, even though "vegetable salad" is better for the young child in terms of achieving the health objective compared to "chicken wings"—this is because the "chicken wing" meal option has a higher salience score due to the food type preference of the young child.

Figure 3C:
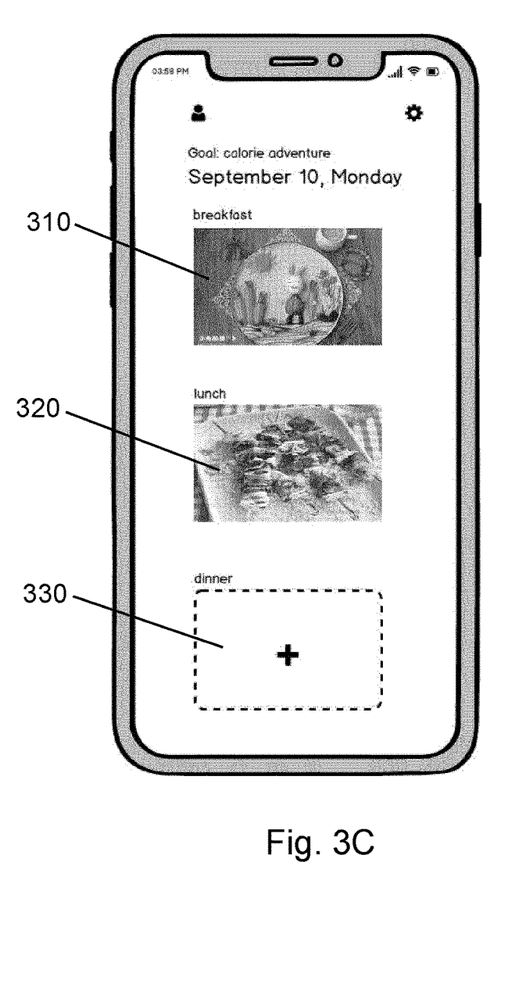
FIG. 3C is another exemplary drawing of the method of FIG. 2 being implemented in a smartphone device.

Once the young child has selected one of the meal options from the image gallery shown in FIG. 3B, the virtual user interface may return to the home screen, as shown in FIG. 3C. FIG. 3C specifically shows an updated home screen in which the lunch 320 has been selected/planned, which is indicated by an image of the selected meal option at the corresponding position in the home screen. In this example, the young child has selected "skewered pork" for lunch, as illustrated by the image of the "skewered pork" option in FIG. 3C.

Figure 3D:
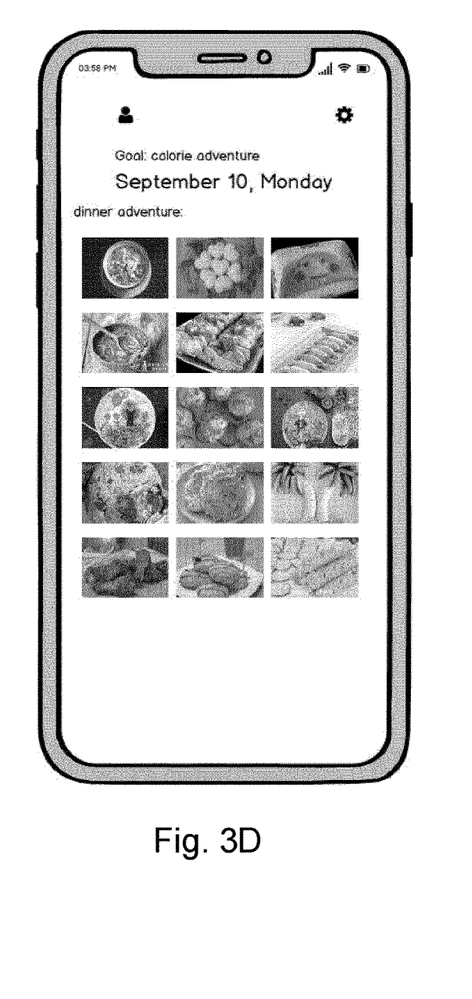
FIG. 3D is another exemplary drawing of the method of FIG. 2 being implemented in a smartphone device.

From the home screen as illustrated in FIG. 3C, the young child may then proceed to select a meal option for his/her dinner of the day by selecting the "+" sign at the virtual user interface which corresponds to the dinner 330 of the day. Similarly, the virtual user interface may then transition to the screen as shown in FIG. 3D which shows a second personalized dietary recommendation. In this example and at this stage, the personalized dietary recommendation includes a plurality of possible meal options for dinner, each being represented by an image of the meal option in an image gallery. In this case, the plurality of meal options, specifically the images corresponding to each of the plurality of meal options, may be displayed in accordance to their respective updated salience scores, such that meal options with higher salience scores are positioned such that they are more likely to be noticed and therefore selected by the young child. The salience scores of the possible meal options for dinner are updated according to an updated balance score, which is determined based on the selection of the "skewered pork" meal option for his/her lunch of the day. In this example, the selection of the "skewered pork" meal option has caused a negative impact on the balance score for the subject and therefore the salience scores are updated so as to prioritize healthier meal options in the image gallery of possible meal options for dinner. Specifically, meal options that are associated with higher dietary energy are displayed lower down in the image gallery so that they are less likely to be noticed and therefore selected by the young child. Once the young child has selected one of the meal options from the image gallery shown in FIG. 3D, the virtual interface may again return to the home screen that is updated with the selected meal option.

Figure 3E:
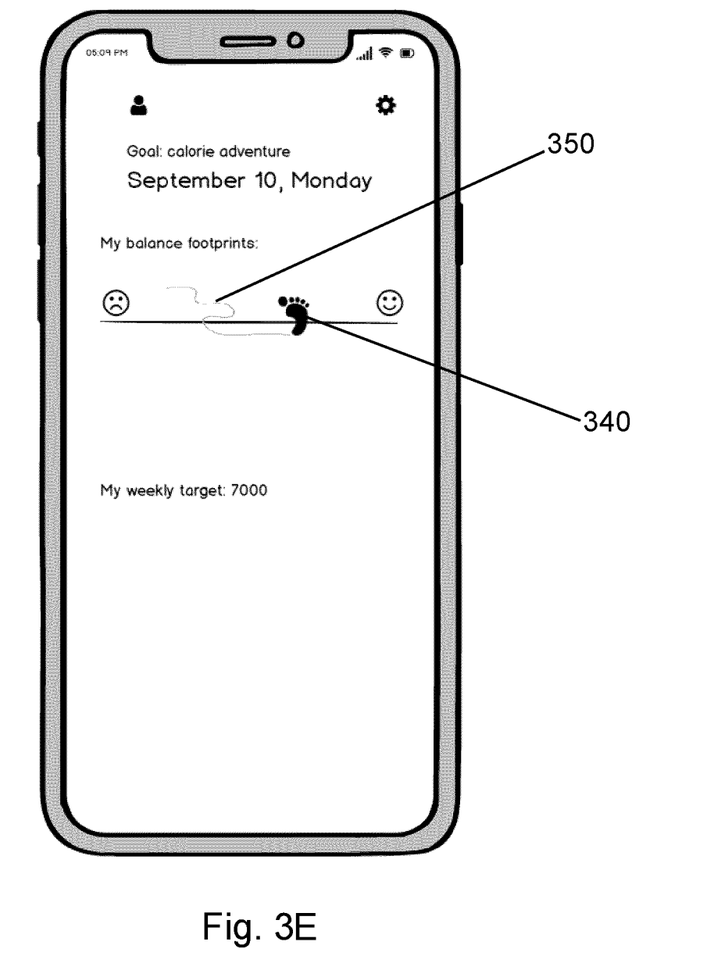
FIG. 3E is another exemplary drawing of the method of FIG. 2 being implemented in a smartphone device.

In the present embodiment, the virtual user interface can further show a progress relating to the balance score of the user in a different screen, an example of which illustrated in FIG. 3E. The progress is presented as a "balance footprint" at the virtual user interface, and the current balance score is represented as a footprint symbol 340 positioned along a horizontal line between a frown emoticon (indicative of unsatisfactory progress) and a smile emoticon (indicative of satisfactory progress), with the middle point of the horizontal line representing a balance score of 0 (i.e. the subject achieving the dietary target in the current periodic interval). The closer the footprint symbol 340 is to the middle point of the horizontal line, the closer the subject is to the dietary target (which, in this case, is a weekly calorie intake target of 700 kcal as displayed), while a position closer to the smile emoticon represents the subject achieving beyond the dietary target and a position closer to the frown emoticon represents the subject not yet achieving the dietary target.

Furthermore, a balance score trail 350 is also presented at the virtual user interface which is representative of the historical balance values since the start of the current periodic interval (i.e. start of the week, in this example). In some embodiments, the virtual user interface may be configured such that points along the balance score trail can be selected so as to access the value of the balance score corresponding to the selected point in time. In this way, a user (e.g. the subject) would be able to discover for example what went wrong in a straightforward way, for example when the balance score trail 350 includes a drastic drop. The user may select the point in the balance score trail corresponding to the drastic drop and review the relevant time information and data associated with dietary consumption of the subject at that point of time. For example, the user may discover that the drastic drop is due to the consumption of 3 hamburgers at 5 pm yesterday by selecting the point corresponding to the drastic drop.

Although the exemplary screen as shown in FIG. 3E shows a balance score trail 350 within a current periodic interval of a week, it will be appreciated that in other embodiments other periodic interval lengths may be used. The length of the periodic interval may be a predetermined value or a value set by via a user input.

It will be appreciated that the embodiment as shown in FIG. 3A to FIG. 3E are exemplary and that in alternative embodiments the plurality of meal options and/or the balance score may be visually represented in a different manner. For example, in alternative embodiments, the balance score may be visually represented in a dashboard consisting of a time series (to present the historical balance score trail) and a bar chart (to present the subject's progress towards the dietary target).

There is thus provided an improved method and apparatus for providing dietary recommendation for a subject, which overcomes the existing problems.

There is also provided a computer program product comprising a computer readable medium, the computer readable medium having computer readable code embodied therein, the computer readable code being configured such that, on execution by a suitable computer or processor, the computer or processor is caused to perform the method or methods described herein. Thus, it will be appreciated that the disclosure also applies to computer programs, particularly computer programs on or in a carrier, adapted to put embodiments into practice. The program may be in the form of a source code, an object code, a code intermediate source and an object code such as in a partially compiled form, or in any other form suitable for use in the implementation of the method according to the embodiments described herein.

It will also be appreciated that such a program may have many different architectural designs. For example, a program code implementing the functionality of the method or system may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other.

An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A computer-implemented method for providing dietary recommendation for a subject, the computer-implemented method comprising:

acquiring a dietary target for the subject, wherein the dietary target is indicative of at least one of: a target amount of a nutrient type and a target amount of dietary energy to be consumed by the subject in a periodic interval;

acquiring data associated with dietary consumption of the subject;

determining a balance score based on the acquired dietary target and the acquired data associated with the dietary consumption of the subject, wherein the balance score is indicative of a difference between a current dietary progress of the subject and the acquired dietary target;

acquiring a plurality of meal options for the subject, wherein each of the plurality of meal options is representative of a suggested meal and comprises dietary information associated with at least one of: an amount of dietary energy of the respective meal option and an amount of nutrient type of the respective meal option, and wherein the nutrient type corresponds to the nutrient type in the dietary target;

acquiring context information associated with at least one of: one or more locations of the subject in the current periodic interval and one or more activities of the subject in the current periodic interval;

receiving a user input indicating a flexibility value, wherein the flexibility value is indicative of a relative degree of user-intended allowed deviation of the dietary consumption of the subject in the current periodic interval from the dietary target;

determining a tolerance value for the current periodic interval based on the dietary target, the flexibility value, the acquired context information, and the balance score, wherein the tolerance value is indicative of an amount of allowed deviation of the dietary consumption of the subject in the current periodic interval from the dietary target;

determining a salience score for each of the plurality of meal options, wherein the determination of the salience score is based at least on the tolerance value and the dietary information of the respective meal option; and generating a personalized dietary recommendation for the subject based on at least one of the determined salience scores, wherein the personalized dietary recommendation is associated with at least one of the plurality of meal options.

2. The computer-implemented method according to claim 1, further comprising controlling a display device to output a visual representation of the generated personalized dietary recommendation for the subject.

3. The computer-implemented method according to claim 2, wherein controlling the display device to output the visual representation of the generated personalized dietary recommendation for the subject comprises controlling the display device to output more than one of the plurality of meal options.

4. The computer-implemented method according to claim 3, wherein the more than one of the plurality of meal options are outputted such that at least one of the following is in accordance with the salience score of the respective meal option: a relative order of the displayed meal options, a relative level of color saturation of the displayed meal options, and a relative size of the displayed meal options.

5. The computer-implemented method according to claim 4, further comprising:

receiving a user input selecting a meal option from the displayed meal options;

determining an updated balance score based on the dietary information of the selected meal option;

determining an updated salience score for each of the plurality of acquired meal options; and generating an updated personalized dietary recommendation for the subject based on at least one of the updated salience scores.

6. The computer-implemented method according to claim 1, further comprising ranking the plurality of meal options based on the determined salience scores, wherein generating the personalized dietary recommendation for the subject is based on the ranking of the plurality of meal options.

7. The computer-implemented method according to claim 1, wherein each of the plurality of meal options further comprises information associated with at least one of: one or more food ingredients in the meal option and one or more food types in the meal option, wherein the computer-implemented method further comprises receiving a user input indicating at least one of: a food ingredient preference of the subject and a food type preference of the subject, and wherein determining the salience score for each of the plurality of meal options is based on the received user input and the information associated with at least one of: the one or more food ingredients in the meal option and the one or more food types in the meal option.

8. The computer-implemented method according to claim 1, wherein generating the personalized dietary recommendation for the subject comprises:

selecting one or more of the plurality of meal options based on the determined salience scores of the respective meal options; and acquiring, for each of the one or more selected meal options, a recipe containing instructions for preparing the respective meal option, and wherein the computer-implemented method further comprises controlling a display device to output a visual representation of the generated personalized dietary recommendation for the subject, wherein controlling the display device to output the visual representation of the generated personalized dietary recommendation for the subject comprises controlling the display device to output the one or more acquired recipes.

9. The computer-implemented method according to claim 1, further comprising:

acquiring updated data associated with the dietary consumption of the subject;

determining an updated balance score based on the acquired dietary target and the acquired updated data associated with the dietary consumption of the subject; and controlling a display device to output a visual representation of the balance score and the updated balance score.

10. The computer-implemented method according to claim 1, wherein acquiring the dietary target for the subject comprises:

acquiring an age of the subject and data associated with a body mass index of the subject;

receiving a user input indicating a health objective of the subject; and determining the dietary target for the subject based on the age of the subject, the data associated with the body mass index of the subject, and the health objective of the subject.

11. The computer-implemented method according to claim 1, wherein acquiring the dietary target for the subject comprises:

acquiring an age of the subject and data associated with a body mass index of the subject;

retrieving, from a database, a standard dietary target for a subject having the same age and the same body mass index as that of the subject; and setting the retrieved standard dietary target as the dietary target for the subject.

12. The computer-implemented method according to claim 1, wherein acquiring the data associated with the dietary consumption of the subject comprises:

acquiring an image depicting a food item consumed by the subject;

performing an image recognition process on the acquired image to identify the food item consumed by the subject; and estimating at least one of: an amount of dietary energy and an amount of nutrient type of the identified food item.

13. A computer program product comprising a computer readable medium, the computer readable medium having computer readable code embodied therein, the computer readable code being configured such that, on execution by a computer or a processor, the computer or the processor is caused to perform the method as claimed in claim 1.

14. An apparatus for providing dietary recommendation for a subject, the apparatus comprising a processor configured to:

acquire a dietary target for the subject, wherein the dietary target is indicative of at least one of: a target amount of a nutrient type and a target amount of dietary energy to be consumed by the subject in a periodic interval;

acquire data associated with dietary consumption of the subject;

determine a balance score based on the acquired dietary target and the acquired data associated with the dietary consumption of the subject, wherein the balance score is indicative of a difference between a current dietary progress of the subject and the acquired dietary target;

acquire a plurality of meal options for the subject, wherein each of the plurality of meal options is representative of a suggested meal and comprises dietary information associated with at least one of: an amount of dietary energy of the respective meal option and an amount of nutrient type of the respective meal option, and wherein the nutrient type corresponds to the nutrient type in the dietary target;

acquire context information associated with at least one of: one or more locations of the subject in the current periodic interval and one or more activities of the subject in the current periodic interval;

receive a user input indicating a flexibility value, wherein the flexibility value is indicative of a relative degree of user-intended allowed deviation of the dietary consumption of the subject in the current periodic interval from the dietary target;

determine a tolerance value for the current periodic interval based on the dietary target, the flexibility value, the acquired context information, and the balance score, wherein the tolerance value is indicative of an amount of allowed deviation of the dietary consumption of the subject in the current periodic interval from the dietary target;

determine a salience score for each of the plurality of meal options, wherein the determination of the salience score is based at least on the tolerance value and the dietary information of the respective meal option; and generate a personalized dietary recommendation for the subject based on at least one of the determined salience scores, wherein the personalized dietary recommendation is associated with at least one of the plurality of meal options.

15. The apparatus according to claim 14, wherein the processor is further configured to control a display device to output a visual representation of the generated personalized dietary recommendation for the subject.

16. The apparatus according to claim 14, wherein the processor is further configured to rank the plurality of meal options based on the determined salience scores, wherein the personalized dietary recommendation for the subject is generated based on the ranking of the plurality of meal options.

17. The apparatus according to claim 14, wherein each of the plurality of meal options further comprises information associated with at least one of: one or more food ingredients in the meal option and one or more food types in the meal option, wherein the processor is further configured to receive a user input indicating at least one of: a food ingredient preference of the subject and a food type preference of the subject, and wherein the salience score for each of the plurality of meal options is determined based on the received user input and the information associated with at least one of: the one or more food ingredients in the meal option and the one or more food types in the meal option.

18. The apparatus according to claim 14, wherein the data associated with dietary consumption of the subject includes at least one of: a type of a food item consumed by the subject, an amount of the food item consumed by the subject, and an amount of a nutrient type in the food item consumed by the subject.

19. The apparatus according to claim 14, wherein the context information includes a type of activity and a duration of activity performed by the subject in the current periodic interval.

* * * * *